United States Patent [19]

Kremer et al.

[11] Patent Number: 4,546,773
[45] Date of Patent: Oct. 15, 1985

[54] APPARATUS TO MEASURE CONICAL THICKNESS

[75] Inventors: Frederic B. Kremer, Bala Cynwyd; Edward R. O'Brien, III, Wayne, both of Pa.

[73] Assignee: Accutome, Inc., Frazer, Pa.

[21] Appl. No.: 607,603

[22] Filed: May 7, 1984

Related U.S. Application Data

[63] Continuation of Ser. No. 227,753, Jan. 23, 1981, abandoned.

[51] Int. Cl.⁴ .............................................. A61B 10/00
[52] U.S. Cl. .................................................. 128/660
[58] Field of Search ...................... 128/660, 24 A, 661, 128/741; 73/609-612, 615, 617; 307/267

[56] References Cited

U.S. PATENT DOCUMENTS

| | | | |
|---|---|---|---|
| 2,708,847 | 5/1951 | Esterman | 128/645 |
| 3,232,099 | 2/1966 | Motchenbacher | 128/648 |
| 3,827,287 | 8/1974 | Boggs et al. | 73/615 X |
| 4,108,165 | 8/1978 | Kopp et al. | 128/24 A X |
| 4,205,682 | 6/1980 | Crock et al. | 128/305 |
| 4,213,464 | 7/1980 | Katz et al. | 128/745 |
| 4,261,367 | 4/1981 | Freese | 128/660 |

FOREIGN PATENT DOCUMENTS

| | | | |
|---|---|---|---|
| 2854514 | 9/1979 | Fed. Rep. of Germany | 128/305 |
| 7513862 | 6/1976 | Netherlands | 128/660 |
| 428743 | 10/1974 | U.S.S.R. | 128/660 |

OTHER PUBLICATIONS

Wells, P. N. T., "Ultrasonics in Clinical Diagnosis", Churchill Livingstone, N.Y. 1977, pp. 87-96.
Giglio, E. J. et al., "A Hand-Held Probe for Acoustic Coupling in UTS Intraocular Distance Measurement in Children", Ame. Jrnl of Optom. V48(1971), pp. 1025-1030.

Primary Examiner—Kyle L. Howell
Assistant Examiner—Francis J. Jaworski
Attorney, Agent, or Firm—Steele, Gould & Fried

[57] ABSTRACT

An apparatus is disclosed for measuring the thickness of the cornea and for regulating the depth of a surgical blade in relation to the local corneal thickness. Corneal thickness is measured by first directing ultrasonic pulses towards the cornea and timing the interval between reflected pulses. The apparatus also includes a pulse stretcher for enlarging the width of the pulse representing the interval between pulses reflected from the inner and the outer surfaces of the cornea, so that the time between pulses can be accurately measured by a conventional, low-frequency electronic clock. The invention further comprises electronic gating means for rejecting spurious pulses.

5 Claims, 16 Drawing Figures

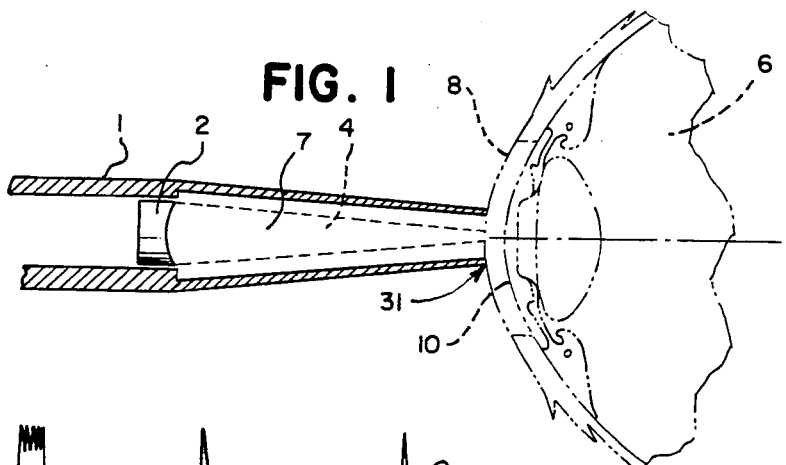
FIG. 1
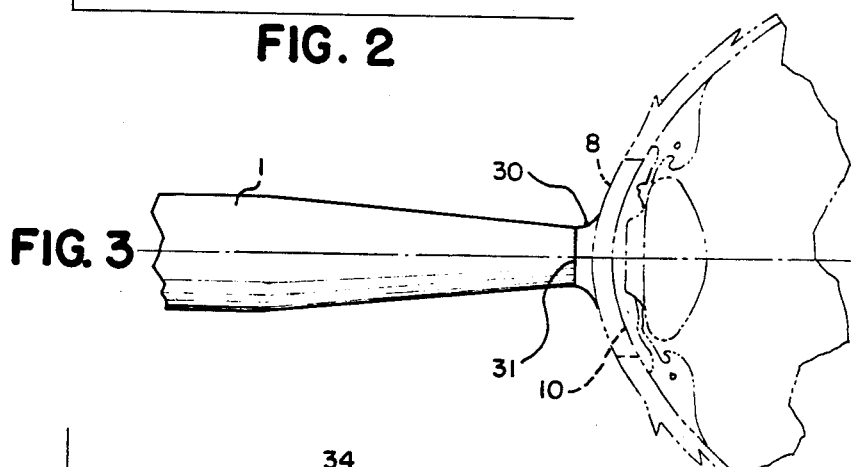
FIG. 2
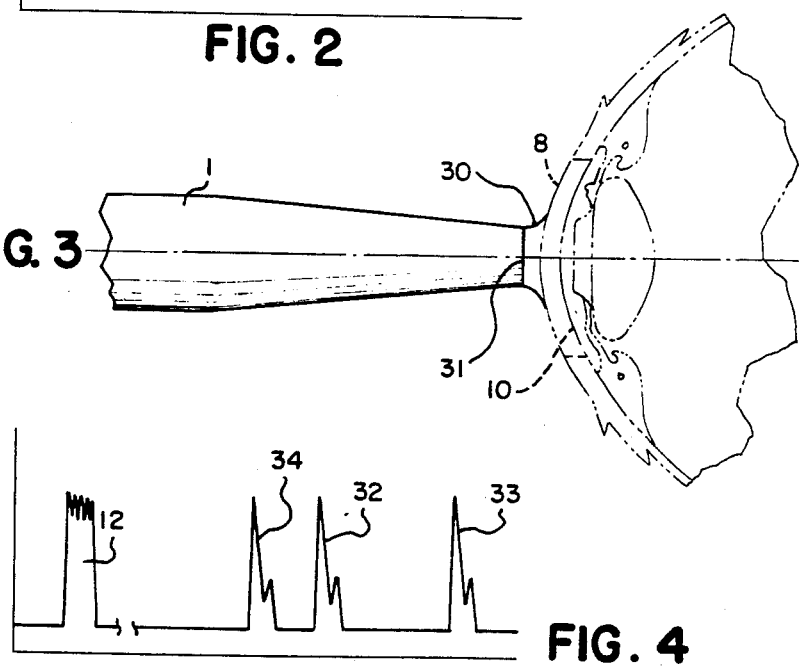
FIG. 3
FIG. 4

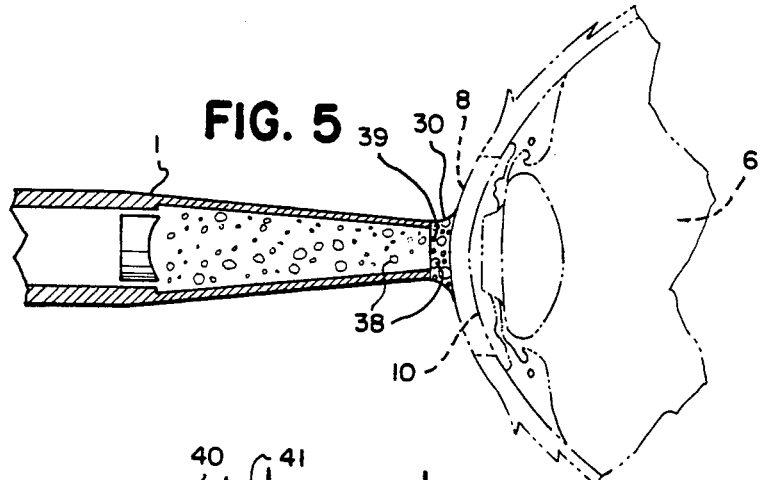
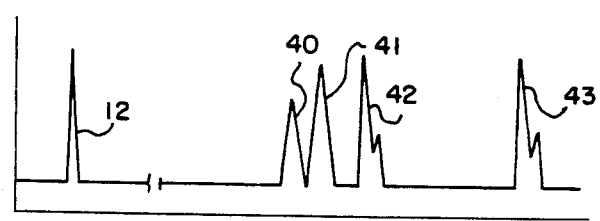
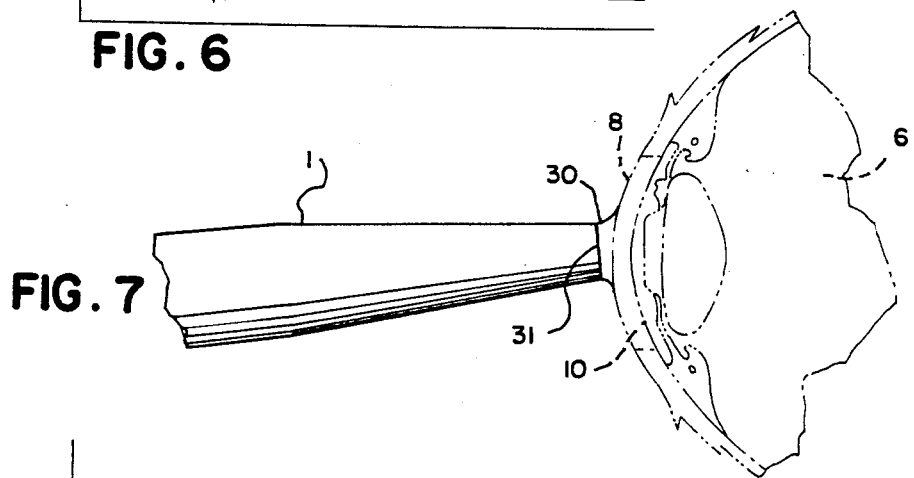

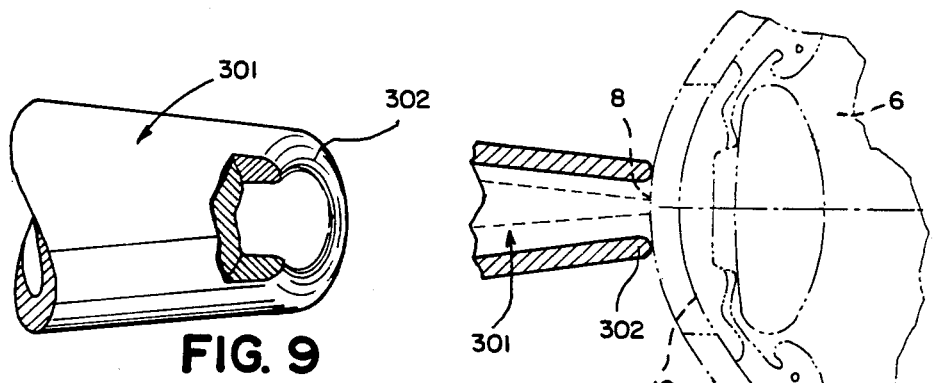
FIG. 9
FIG. 10
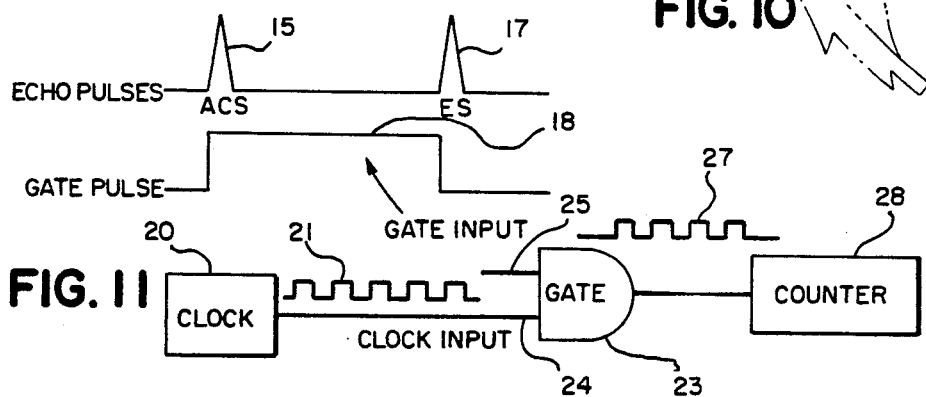
FIG. 11
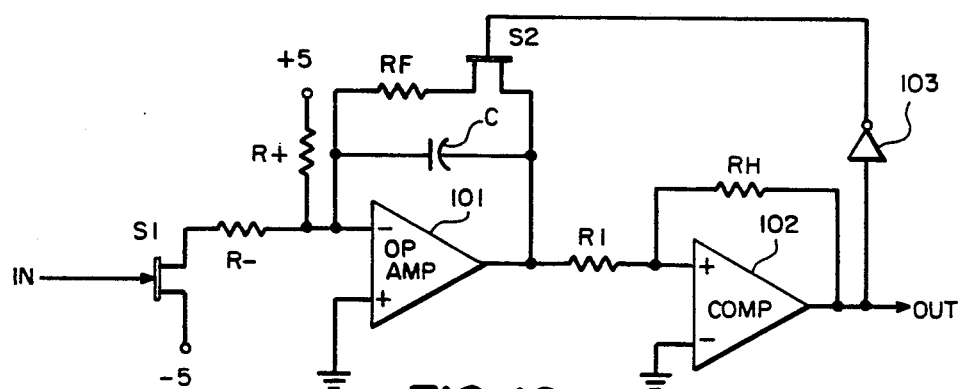
FIG. 12

APPARATUS TO MEASURE CONICAL THICKNESS

This is a continuation of application Ser. No. 227,753, filed 1/23/81 and now abandoned.

BACKGROUND OF THE INVENTION

The present invention comprises an apparatus and method for performing surgery on the cornea by electronically measuring the thickness of the cornea and automatically or manually adjusting the depth of a surgical blade in accordance with the measured thickness. Surgical treatment of the eye in numerous instances requires a partial thickness incision of the cornea. Examples where such incisions are required, include radial keratotomy, relaxing incisions, wedge resections, lamellar keratoplasty, tumor excisions, etc. The apparatus disclosed herein improves the safety and accuracy with which these procedures can be executed. Although the apparatus will have value in the performance of other procedures, its initial application will be in the area of radial keratotomy.

Radial keratotomies involve the reshaping of the cornea to improve refractive error. In 1974, Fyodorov developed a technique in Moscow for making partial thickness radial corneal incisions for the reduction of myopia (nearsightedness). Since that time, this procedure has been performed on approximately 1500 persons in the Soviet Union. A review of the risks and benefits of this procedure is expected to be published in the Annals of Opthamology. It is anticipated that a major problem inherent in the procedure will be the possibility of corneal perforation. If such perforation occurs, there is a risk of infection and ensuing visual loss. One purpose of the present invention is therefore to reduce greatly this risk.

Another problem in the performance of corneal surgery involves the regulation of depth of the incisions which must be precise in order to correct refractive error accurately. The apparatus disclosed herein helps in this regard.

In the prior art, for example, U.S. Pat. No. 4,154,114, ultrasonic pulses have been employed to determine distances between points in the body. However, most instruments previously used to measure distances within the eye utilize an ultrasonic probe having a tip which touches the cornea in a manner which can introduce small but significant errors. These instruments use the probe tip echo to represent the anterior cornea surface. But in fact, the probe tip is seldom totally coincident with the surface of the cornea, and so the opportunity for an introduced error is possible in the measurement.

Another problem in the use of ultrasonic techniques to measure corneal thickness is the fact that the cornea is extremely thin. Pulses reflected from the anterior cornea surface (i.e. the outer surface) and the endothelium surface (i.e. the inner surface) are separated by such a short interval as to make it difficult to accurately measure the time interval between pulses using classical techniques. Although most ocular element distances are of the order of 2-25 mm, the human cornea is only about 0.4-1.0 mm thick, so the time between echo pulses can be as short as 500 nanoseconds. In order to measure the distance between pulses, a clock frequency of approximately 80 MHz would be required instead of the typical 8 MHz clock frequency used in present ocular element measurement systems.

The requirement of a high frequency clock introduces several technical problems. Standard transistor-transistor logic (TTL) elements can no longer be used in gating and counting circuits because the maximum operating frequency for TTL is 40 MHz. Secondly, emitter-coupled logic (ECL) could be used, but ECL is very susceptible to noise transients and the complexity of the circuit board layout is greatly increased.

One approach that has been suggested for solving the high clock frequency problem discussed above would be to average individual measurement cycles at a lower clock rate. With this method, instead of the counter being reset after each single real-time pulse measurement, the counter is allowed to count up for a predetermined number of pulse echo cycles (such as 100) and therefore, the clock frequency could be decreased. This approach presents at least three problems. First, real-time measurements are not possible. Secondly, the accuracy of the measurement is a function of the number of samples taken. Greater accuracy can sometimes be obtained with a larger sample, but at the expense of more time. In certain approaches to corneal surgery, this extra time may not be available, as it is desired to adjust the cutting blade almost instantaneously based on the local measured corneal thickness. Thirdly, to use a statistical averaging approach, it is mandatory that the clock frequency be totally independent of the circuit which generates the ultrasonic pulse signals. Due to the radio frequency (rf) energy which is emitted while generating these pulses, it is extremely difficult to prevent this energy from influencing the counter frequency, thereby degrading the statistical average.

SUMMARY OF THE INVENTION

The present invention solves the above-described problems by providing an apparatus and method for automatically adjusting the depth of the cutting blade in response to electronic signals representing the local thickness of the cornea. A pulse of energy, preferably an ultrasonic pulse, is directed towards the eye from a hand-held transducer, and reflected pulses are received. The ultrasonic transducer has a plastic water filled probe tip which transmits the ultrasonic pulses directly to the anterior corneal surface (ACS). The ACS therefore is the first pulse to be received. This pulse arms a gate which then expects to receive a reflected pulse from the posterior corneal surface (PCS). Therefore, if a reflected pulse from the anterior cornea surface is received within the anticipated time window, the apparatus then prepares to receive a pulse reflected from the posterior corneal (endothelial) surface (PCS), also within a reasonable time window. The time interval between the reflected pulses from the anterior corneal surface (ACS) and the posterior corneal surface (PCS) represents the thickness of the cornea.

The two reflected pulses, from the ACS and the PCS, are converted into a single gate pulse which begins with the ACS pulse and ends with the PCS pulse. This gate pulse is then stretched by a predetermined factor, such as 10, and its width is measured by counting the number of pulses emitted by an electronic clock during the time that the stretched gate pulse is present. The width is converted to a corresponding distance (based on the acoustic velocity of the cornea) and is displayed digitally.

After the corneal thickness has been accurately measured in the above manner, this measurement may be used in two different ways. In the first, a separate hand-held blade may be manually adjusted to an appropriate length and in the second, an electronic signal representing the instantaneous measured thickness of the cornea at the position of the probe can be used to automatically control the cutting depth of an automated blade. The cutting depth of the blade can be set by several different means—including either an electric motor, a pneumatic means, a hydraulic means, or an electro-magnetic means. The blade can be adjusted to cut at a constant depth (as measured from the anterior corneal surface) or at a constant percentage of the total corneal thickness, or at a constant distance from the posterior corneal surface. In the automatic configuration, the probe and blade assembly is moved over the eye, corneal thickness is repeatedly and automatically remeasured and the cutting blade is automatically adjusted accordingly. Thus, in the automatic configuration, the apparatus performs the above-described steps a great many times, and the time required for each cornea measurement and blade adjustment cycle must therefore be extremely short.

It is therefore an object of the present invention to provide an improved method of performing corneal surgery which is both safe and accurate.

It is a further object of the present invention to provide an apparatus which measures the corneal thickness in a manner substantially free from errors due to spurious reflected pulses, wherein said measurement can be used to regulate the depth of a cutting blade.

It is a further object of the present invention to provide a pulse stretcher which permits the measurement of corneal thickness using conventional techniques.

It is a further object of the present invention to provide an apparatus wherein rapid and repeated measurements of corneal thickness are made and which are used to control the instantaneous position of a surgical cutting blade.

It is a further object of the present invention to provide a method of performing corneal surgery using the apparatus described above.

Other objects and advantages of the present invention will be apparent to those skilled in the art from a reading of the following detailed description of the invention, and appended claims, and by referring to the accompanying drawings wherein like reference characters refer to similar parts throughout and wherein:

BRIEF DESCRIPTION OF THE DRAWINGS

FIG. 1 is a cross-sectional view of the probe touching the surface of the eye in an idealized, hypothetical application, wherein the end of the probe corresponds precisely to the outer surface of the eye.

FIG. 2 is a diagram showing the relative amplitudes and shapes of the pulse directed towards the eye and the two reflected pulses in the idealized configuration of FIG. 1.

FIG. 3 is an elevational view of a modified ultrasonic probe applied to the eye, wherein there is a thin layer of liquid film between the probe tip and the cornea and wherein the probe is solid.

FIG. 4 is a diagram showing the relative amplitudes of the pulses reflected from the eye, in the configuration of FIG. 3.

FIG. 5 is a side elevational view of a probe applied to the eye wherein there are bubbles or foreign matter trapped in the liquid.

FIG. 6 is a diagram showing the amplitudes of the reflected pulses resulting from the configuration of FIG. 5.

FIG. 7 is a side elevational view of a probe touching the eye wherein the probe tip is slightly tilted, thereby yielding another source of error.

FIG. 8 is a diagram showing the relative amplitudes of the reflected pulses as observed in the configuration of FIG. 7.

FIG. 9 is a fragmentary perspective view of the probe tip which is applied to the surface of the eye, partially broken away to expose interior construction details.

FIG. 10 is a cross-sectional view of the probe tip as applied to the cornea.

FIG. 11 is a block diagram indicating the conventional means by which reflected pulses are converted into a measurement of corneal thickness.

FIG. 12 is a schematic circuit diagram showing the pulse stretcher of the present invention.

DETAILED DESCRIPTION OF THE INVENTION

Figure 13:
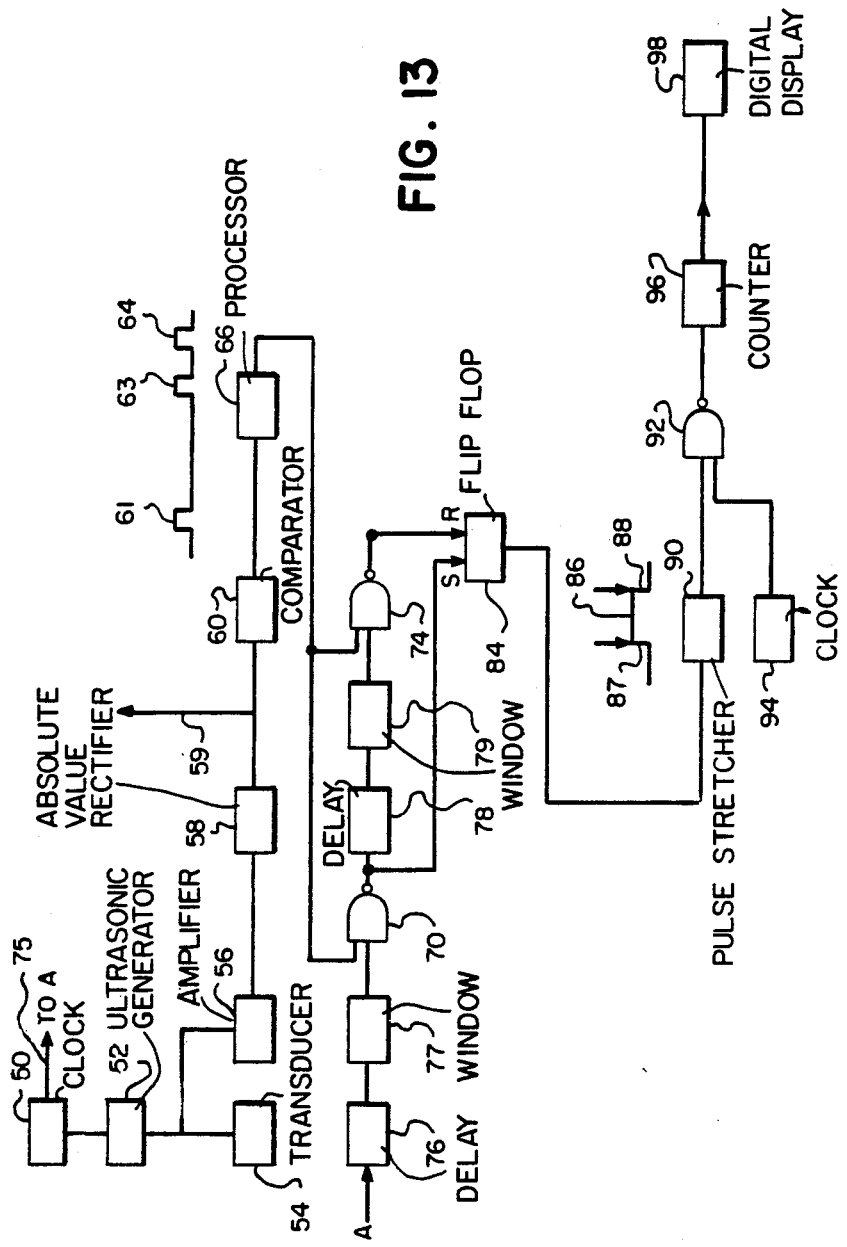
FIG. 13 is a block diagram of the preferred embodiment of the present invention.

Before describing the present invention in detail, it is helpful to explain with more specificity the particular problems which need to be solved in the performance of corneal surgery.

FIGS. 1, 2 and 11 illustrate the ideal configuration for measuring corneal thickness. In FIG. 1 the probe 1 contained a forward ultrasonic transducer 2 which emits ultrasonic waves, as indicated by the dashed lines 4, through a water medium 7, towards the eye 6. Preferably, the water medium 7 is distilled water, which water will remain within the interior cavity defined by the probe tip through the action of normal surface tension of the water. Ultrasonic pulses are reflected from the anterior corneal surface 8 (ACS) and from the posterior corneal surface 10 (PCS) (i.e. the inner surface) and are reconverted into electrical energy at the transducer 2. It should be noted that in the ideal configuration of FIG. 1, the end of probe 1 lies precisely along anterior cornea surface 8.

FIG. 2 shows the sequence of pulses resulting from the arrangement of FIG. 1. Pulse 12 represents the initial pulse (main bang) which is directed towards the eye; pulse 14 represents the first reflected pulse, i.e., the pulse from the anterior cornea surface; pulse 16 represents the reflection from the posterior cornea surface. Clearly, the distance between pulses 14 and 16 represents the thickness of the cornea.

There is a problem which can arise when the idealized configuration of FIGS. 1, 2 and 11 is put into practice. As illustrated in FIG. 5 wherein bubbles 38 and/or foreign matter 39 may be trapped in the water 7 or liquid film 30 and may further cause distortion in the received pulses. As shown in FIG. 6, intermediate peaks 40 and 41 may also be observed, these peaks being caused by reflections from the bubbles and foreign matter. The pulses 42 and 43 correspond to the pulses 14 and 16 of FIG. 2, respectively, but may be reduced in amplitude, due to the poor transition through the mixture (liquid, bubbles and/or foreign matter).

An advantage inherent with the idealized configuration of FIG. 1 is illustrated in FIG. 7. The probe 1 is seen to be slightly tilted so that the cornea echo pulse would be greatly reduced in magnitude. The shape of such a reflected pulse is illustrated in FIG. 8. The pulse 46 and the pulse 47 represent reflections from the cornea. This reduction in pulse amplitude would not allow the necessary gates to be triggered, thus avoiding a non-perpendicular and erroneous reading from being taken.

Another advantage of the liquid filled probe tip is inherent in the design of FIG. 1. Should the tip of probe 1 not actually rest precisely on the corneal surface 8, there may be a liquid film similar to the film 30 formed between the tip 31 of probe 1 and the cornea surface 8. Because the probe 1 is liquid filled, only pulses 32 and 33 as shown in FIG. 4 from the anterior cornea surface 8 and the posterior surface 10, will be generated. Spurious pulse 34 would not be generated. This spurious pulse would result, however, with the solid probe tip. See FIG. 3.

As best seen in FIGS. 9 and 10, in the preferred embodiment, the probe 301 is provided with a forward ring or tip 302 in position to contact the anterior cornea surface 8 in substantially circular overall contact to thereby discourage the generation of undefined cornea echo pulses 40 and 41 (FIG. 6) and to define a definite initial pulse 14 (FIG. 2) representing the anterior cornea surface 8.

FIG. 11 illustrates how the reflected pulses are converted into a usable numerical output. The pulses 15 and 17, which are schematically illustrated in FIG. 11, correspond to the pulses 14 and 16 of FIG. 2 and represent the anterior cornea surface and the posterior cornea surface as described above. Through appropriate circuitry (to be described below), these pulses are converted into a gate pulse 18, which begins with the anterior cornea surface pulse and ends with the posterior cornea surface pulse. A clock 20, which generates a constant string of pulses 21 of equal amplitude and spacing, is connected to AND gate 23 at the input line 24. The input line 25 is connected to the source of the gate pulse 18. When the gate pulse 18 begins, the AND gate 23 allows clock pulses to pass through the gate and the output of the gate 23 will be the pulses 27. These output pulses 27 are counted in the usual manner by the counter 28. The number of such pulses therefore represents the width of the gate pulse 18, which in turn represents the thickness of the cornea.

As indicated above, still another problem encountered in measurement of corneal thickness by ultrasonic techniques is caused by the extreme thinness of the cornea. The actual time between the pulses 15 and 17 in FIG. 11 would actually be only in the range of 0.4 to 1.2 microseconds. In order to determine accurately the length of the gate pulse 18, it is necessary to use a clock having pulses 21 with widths substantially shorter than that of the pulse 18. Therefore, in order to use the configuration of FIG. 11, it is necessary to provide a clock with a pulse frequency of 80 MHz, which is impractical for the reasons discussed earlier.

A block diagram of an apparatus which solves the above problems is illustrated in FIG. 13. This apparatus is an ultrasonic pachometer, or "corneometer". The "corneometer" functions as follows: Pulses are generated by the clock 50, which preferably generates pulses having a frequency of 5 kHz. The clock pulses are used to excite an ultrasonic generator 52 which drives a transducer 54 which converts electrical pulses into ultrasonic energy in known manner. When the ultrasound beam from the transducer encounters a surface, or object, part of the energy is reflected back to the transducer. These reflected echo pulses are converted to electrical energy again by the transducer 54, and the echo pulses are fed into the amplifier 56 and to the absolute value rectifier 58. The line 59 may be connected to a cathode ray tube (not shown) if it is desired to display the echo pulses at this stage. The echo pulses are then fed through a comparator 60 which compares the echo pulse with a threshold value so as the detect the echo pulses from noise. The configuration of the detected pulses that would be expected is illustrated schematically as the pulses 61, 63 and 64. Pulse 61 represents the so-called main bang, the original ultrasound pulse which is directed towards the eye. Pulse 63 represents the reflected echo pulse from the cornea anterior surface and the pulse 64 is the echo pulse reflected from the cornea posterior surface or endothelium layer. The output of the comparator 60 is converted into pulses having a width of 100 nanoseconds by the processor 66 which receives and shapes the pulses properly for further processing. The output of the processor 66 is connected to one input of each of the AND gates 70 and 74.

Meanwhile, the output of the clock 50 is extracted along the line 75 (designated by the label "TO A") and is connected to the point labeled "A", where it is passed through a 6-microsecond delay 76 corresponding to the nominal time required for the reflected echo pulse from the cornea anterior surface to reach the transducer and a 1-microsecond window 77. The 1-microsecond window allows for dimensional variations of the probe tip. During the 1-microsecond window, AND gate 70 will have a positive output only when pulse 63 is detected. A pulse not arriving within the proper window is treated by the circuit as a spurious pulse, and is discarded. If the pulse is spurious, the absence of a positive output in AND gate 70 will inhibit further measurement of corneal thickness during this particular cycle of operation.

The output of the AND gate 70 is passed through a 300 nanosecond delay 78 and a 1.5 microsecond window 79, the output of which is ANDed with the posterior cornea surface echo pulse 64. The AND gate 74 will show a positive output upon detection of the posterior surface.

The output of the AND gate 70 is connected to the SET input of the flip-flop 84 and the output from the AND gate 74 is connected to the RESET side of flip-flop 84. The output of the flip-flop 84 is therefore the gate pulse 86, whose leading edge 87 represents the beginning of the cornea anterior surface echo pulse and whose trailing edge 88 represents the cornea posterior surface echo pulse. The gate pulse 86 corresponds to the gate pulse 18 shown in FIG. 11, but of course, the gate pulse 86 is, in practice, very narrow due to the thinness of the cornea, as described above.

The gate pulse 86 is then directed into the pulse stretcher 90 which increases the width of the gate pulse by a predetermined factor, preferably ten. As illustrated in FIG. 13, the output of pulse stretcher 90 is connected to an input of the AND gate 92. The other input of the AND gate 92 is an 8.1 MHz clock 94 which generates pulses in a manner similar to that of the clock 20 in FIG. 11. Because the pulses produced by the pulse stretcher 90 are ten times wider than they were originally, the clock 94 can operate at the relatively low frequency of 8.1 MHz and retain the desired accuracy and resolution in the readout. The pulses leaving the AND gate 92 are counted in the counter 96, and the output of the counter 96 is displayed in a visual digital display unit 98 in an appropriate manner.

The construction details of the pulse stretcher 90 are shown in FIG. 12 in schematic form. The essential part of the operation is controlled by solid state switches S1 and S2. During quiescent conditions, switch S1 is turned off, switch S2 is turned on, and the operational amplifier 101 has an output which settles to a small negative voltage determined by $-(RF/R+)$ 5 volts. The solid state switches can be field effect transistors, but more preferably are a combination of field effect transistors to provide better isolation and sharper switching response. The slightly negative output of the operational amplifier 101 biases the comparator 102 low, which in turn keeps the solid state switch S2 closed by virtue of the inverter 103.

When an input pulse enters the pulse stretcher 90, the switch S1 closes and because $R-$ is smaller than $R+$, the output of the operational amplifier 101 becomes positive. At the moment the operational amplifier output passes through zero (from its slightly negative equilibrium state), the output of comparator 102 goes high opening switch S2 so that the operational amplifier 101 becomes an integrator, due to the influence of the capacitor C.

When the input pulse ends, the switch S1 opens, so that the input to the operational amplifier 101 (which is now integrating) is driven positive by the voltage applied through $R+$. This positive input causes the integrator output to tend toward zero. Until the integrator becomes slightly negative again, the output of the comparator 102 stays high, maintaining the positive output and keeping the switch S2 open. The operational amplifier 101 (acting as an integrator) eventually goes slightly below zero to overcome the current through the comparator hysteresis resistor RH and the comparator output drops low, ending the positive output.

The output of the pulse stretcher 90 can deviate from the desired output for two reasons; namely, gain error and offset error. This output can be described by the equation $$T_o = KT_I + L$$

where $T_o$ is the output pulse width, $T_I$ is the input pulse width, K is the time multiplication factor (gain) and L is the time offset. Ideally, $K=10$ and $L=0$.

To change L, RF is changed. The resistor RF sets the equilibrium state and therefore determines how much of the input pulse is spent in overcoming this negative state before the output starts. L will be zero when this effect exactly cancels the termination delay caused by the hysteresis resistor RH.

The value of K is changed by changing $R-$. The resistor $R-$ determines how fast the input pulse is integrated and therefore, the point from which the current through $R+$ must restore zero. This adjustment capability for gain provides the additional feature that the differences in the velocity of sound through different materials can be compensated for by adjusting the gain as compared to the conventional method of changing the counter clock frequency.

Figure 14:
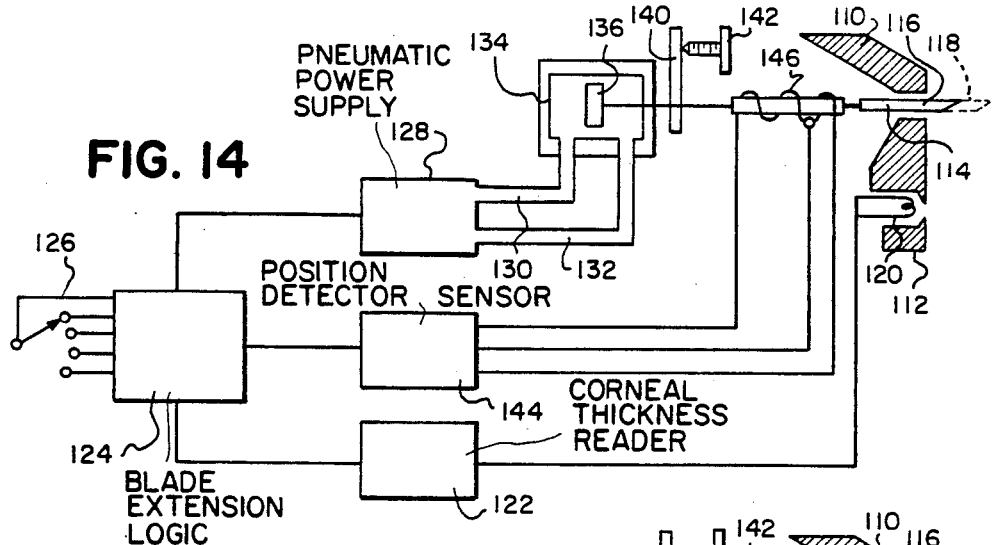
FIGS. 14–16 diagrammatically illustrate three separate systems to automatically extend or retract the cutting blade.
Figure 15:
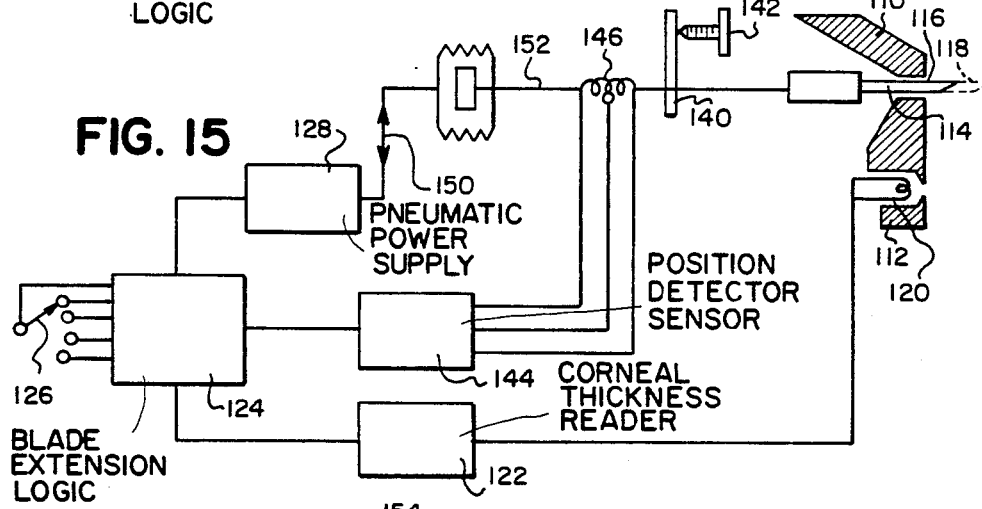
Figure 16:
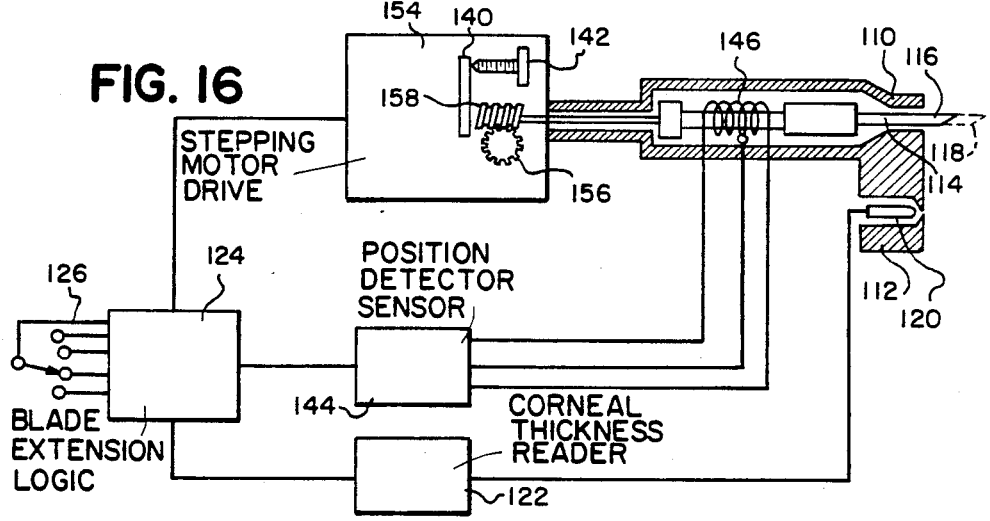

Referring now to FIGS. 14, 15 and 16, there are diagrammatically illustrated three approaches to show various systems that could be employed to automatically extend or retract a cutting blade 114 in response to changes in thickness of the cornea as measured by apparatus hereinbefore described. In each instance, the tip 110 of the cutting instrument 112 houses both the blade 114 and the ultrasonic probe 120 in side by side juxtaposition whereby the blade 114 will be automatically movable between respective retracted positions 116 as illustrated in full lines, to extended positions, as shown in broken lines, in response to variations in the cornea thickness as detected by the ultrasonic probe 120.

As illustrated in FIG. 14, the echo pulses from the ultrasonic probe 120 are received at the corneometer thickness reader 122 wherein the cornea thickness is transmitted to the blade extension logic 124. Preferably, the blade extension logic is equipped with a manually preset cornea percent penetration selection switch 126 so that the cutting blade can always be maintained at a cutting depth corresponding to a predetermined, constant precentage of the thickness of the cornea. Optionally, the blade 114 could be adjusted automatically to maintain a predetermined distance from the posterior corneal surface or to cut at a constant depth, as measured from the anterior corneal surface. The blade extension logic powers a pneumatic power supply 128, which through the feed and return lines 130, 132 functions the cylinder 132 to control reciprocal movement of the piston 136. The piston rod 138 directly connects to the cutting blade 114 to move the blade between its retracted position 116 and extended position 118 substantially instantaneously in response to variations in the actual corneal thickness, as detected by the ultrasonic probe 120. A safety stop 140 is affixed to the piston rod 138 in position to be engaged by the adjustable set screw 142 to precisely set the extended limit of the blade extended position 118. Optionally, if so desired, a position detector sensor 144 can be employed to continuously sense the position of the cutting blade as detected by the sensing coil 146.

In the embodiment illustrated in FIG. 15, cutting instrument 112, blade 114, ultrasonic probe 120, corneal thickness reader 122, blade extension logic 124, cornea percent penetration selection switch 126 and pneumatic power supply 128 are identical to the apparatus shown in FIG. 14. In this embodiment, the power supply 128 feeds a bellows 148 through an in-out valve as represented by the two-headed arrow 150 to reciprocate the cutting blade affixed extension arm 152. Accordingly, the blade 114 can be readily moved in response to signals from the blade extension logic 124. A safety stop 140 with set screw 142 and position detector sensor can be provided in the manner above set forth.

In the embodiment illustrated in FIG. 16, the cutting instrument 112, blade 114, ultrasonic probe 120, corneal thickness reader 122, blade extension logic 124 and cornea percent penetration selection switch 126 are identical to the apparatus shown in FIGS. 14 and 15. As illustrated, the blade extension logic 124 controls extension and retraction of the cutting blade 114 through a stepping motor drive 154 which may include a driving sprocket 156 and screw type blade extension cable 158. A safety stop 140 and adjustable set screw 142 are provided in known manner to precisely limit the maximum possible depth of cut. Optionally, a position detector sensor 144 can be employed in conjunction with the sensing coil 146 to monitor the exact position of the cutting blade 114 relative to the cutting instrument tip 110.

It is understood that the above description of the preferred embodiment is only illustrative of the manner in which the present invention can be practiced. Other variations are possible, for example, the pulses could be electromagnetic and not ultrasonic. The precise manner in which the probe and blade assembly is constructed can be varied. The mechanism for advancing the blade may use electromagnetic, hydraulic, or pneumatic force. It is understood that these and other variants are included within the scope of the claims appended hereto.

What is claimed is:

1. Apparatus for measuring the thickness of a cornea having an anterior surface and a posterior surface comprising means for directing pulses of ultrasonic energy toward the said cornea surfaces to create a first reflected pulse from the anterior cornea surface and a second reflected pulse from the posterior cornea surface;

time window means for receiving the first and second reflected pulses only if they arrive within a predetermined expected time interval;

means for measuring the time interval between the first and second reflected pulses, the means for measuring comprising means to convert the pulses to a gate pulse and means to stretch the gate pulse, the means to stretch the gate pulse comprising means for integrating the gate pulses, said means for integrating comprising an input and an output, comparator means having an input and an output, said comparator means being connected to the output of said means for integrating, and means for controlling the operation of said means for integrating, said controlling means being itself controlled by the output of said comparator means;

means for inhibiting the measurement of time intervals before the first reflected pulse which do not arrive within the said predetermined expected time interval and after the second reflected pulse which do not arrive within the said predetermined expected time interval; and means for converting the time interval between the first and second reflected pulses into an equivalent measured distance.

2. The apparatus of claim 1 wherein said integrating means comprises an operational amplifier.

3. The apparatus of claim 2 wherein the means for controlling comprises an electronic switch, said switch having two poles and being connected to be actuated by the inverted output of the comparator means.

4. The apparatus of claim 3 further comprising a resistor connected between one input of the means for integrating and one pole of the switch, the other pole of the switch being connected to the output of the means for integrating, whereby the switch is capable of connecting the resistor across and disconnecting the resistor from the means for integrating.

5. The apparatus of claim 4 further comprising a hysteresis resistor connected between the input and output of the comparator means.

* * * * *